United States Patent [19]

Mobilio et al.

[11] Patent Number: 5,216,165
[45] Date of Patent: Jun. 1, 1993

[54] N-SUBSTITUTED AMINOQUINOLINES AS ANALGESIC AGENTS

[75] Inventors: Dominick Mobilio, Franklin Park, N.J.; John H. Musser, Alameda, Calif.

[73] Assignee: American Home Products Corporation, New York, N.Y.

[21] Appl. No.: 855,397

[22] Filed: Mar. 20, 1992

Related U.S. Application Data

[63] Continuation-in-part of Ser. No. 592,411, Oct. 3, 1990, abandoned.

[51] Int. Cl.⁵ .......................................... C07D 401/12
[52] U.S. Cl. .................................. 546/160; 516/19; 516/161; 516/216; 516/223
[58] Field of Search ........................................ 546/160

[56] References Cited

U.S. PATENT DOCUMENTS 4,235,908 11/1980 Boyle ..................... 546/160

Primary Examiner—C. Warren Ivy
Assistant Examiner—James H. Turnipseed
Attorney, Agent, or Firm—George Tarnowski

[57] ABSTRACT

There are disclosed compounds of the formula

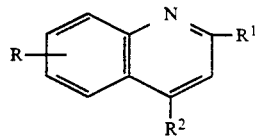

wherein
R is hydrogen, halo or trifluoromethyl;
$R^1$ is hydrogen or X;
$R^2$ is hydrogen or X; with the proviso that when $R^1$ is X, $R^2$ is hydrogen, and when $R^1$ is hydrogen, $R^2$ is X;
X is the moiety

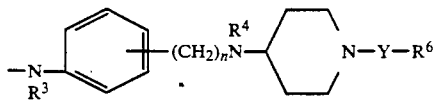

wherein
$R^3$ is hydrogen or lower alkyl;
$R^4$ is hydrogen or

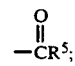

$R^5$ is hydrogen, alkyl of 1–16 carbon atoms, phenyl, phenylloweralkyl or perfluoroloweralkyl;
Y is CO or a bond;
$R^6$ is lower alkyl, cycloloweralkyl, arylalkyl, —$(CH_2)_m$-cycloloweralkyl,

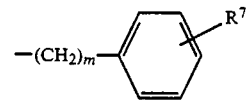

or —$(CH_2)_o CONR^8R^9$ or, in the case when Y is CO, phenyl;
$R^7$ is hydrogen or

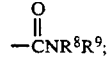

$R^8$ and $R^9$ are, independently, hydrogen, lower alkyl, cycloloweralkyl or $R^8$ and $R^9$ together with the nitrogen atom to which they are attached form a 5–8 membered saturated monoazacyclic ring;
m is 1–3;
n is 1–3;
o is 1–10;

and the pharmacologically acceptable salts thereof and, which by virtue of their ability to antagonize bradykinin, are analgesic agents useful in the treatment and management of pain.

18 Claims, No Drawings

N-SUBSTITUTED AMINOQUINOLINES AS ANALGESIC AGENTS

This is a continuation-in-part of U.S. Ser. No. 07/592,411, filed Oct. 3, 1990, now abandoned.

The nonapeptide bradykinin has been shown to cause pain in man when applied intradermally, intra-arterially, intraperitoneally or to a blister base [see Kantor et al., *Proc. Soc. Exp. Biol. Med.*, 126, 505–507 (1967)] and it has been demonstrated that it is one of the most potent pain-producing substances [see Keele and Armstrong, *Substances Producing Pain and Itch*, London, 1964]. Thus, in rats and mice, an intraperitoneal injection of bradykinin induces writhing [see Collier et al., *Br. J. Pharmac, Chemother.*, 32, 295–310 (1968) and Loux et al., *Arzneim.-Forsch. Drug Res.*, 28(II), 1644–47 (1978)], while an intra-arterial injection in cats and dogs likewise elicits a measurable pain response [see Guzman et al., *Arch. Int. Pharmacodyn.*, 149, (3–4), 571–88 (1964)].

Bradykinin is released in response to tissue injury. Thus, polymorphonuclear leukocytes migrate to the site of injury and release proteases, which in turn act on 2-globulins to form bradykinin. This bradykinin binds to the peripheral pain receptors at the nerve endings and cause the nerves to fire. These nerve impulses, via the spinal cord, cause the release of substance P, which, in turn, amplifies the pain signals through an increase in nerve firing. Substance P also binds to the mast cells, stimulating histamine release, which causes further inflammation, thereby enhancing the generation and propagation of pain impulses [see Kantor et al., *Am. J. Med.*, 80 (suppl. 3A), 3–9, (1986) and Shibata et al., *Japan J. Pharmacol.*, 41, 427–8 (1986)].

At the same time, bradykinin acts directly on receptors of the capillary wall to increase vascular permeability, with consequent plasma exudation and increased leukocyte diapedesis. As a result, inflammation is perpetuated and further mediators, like prostaglandins, histamine and bradykinin, are released, all of which serve to further intensify the pain impulses [see Yaksh et al., *Acetylsalicylic acid: New use for an old drug*, Raven Press, New York, 1982, p. 137–151)].

Bradykinin also binds to mast cells, thereby triggering the release of histamine, with consequent additional pain and inflammation, as well as the cascade of reactions leading to the formation of more prostaglandins [see Regoli et al., *Pharmacol. Rev.*, 32(1), 1–46 (1980)].

Consequently, by direct effects on cell membranes and by indirect effects on the release of other mediators, bradykinin triggers, transmits and amplifies the pain impulses from the peripheral to the central sites. Therefore, it is clear that a bradykinin antagonist can be advantageous in the treatment and management of pain by preventing the bradykinin-mediated transmission of the pain signal from the peripheral receptor site to the central nervous system. It has been found that the compounds of the invention, as antagonists of bradykinin, are analgesic agents which are useful in the treatment and management of pain.

The invention provides novel compounds of the formula

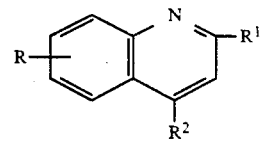

wherein
R is hydrogen, halo or trifluoromethyl;
$R^1$ is hydrogen or X;
$R^2$ is hydrogen or X; with the proviso that when $R^1$ is X, $R^2$ is hydrogen, and when $R^1$ is hydrogen, $R^2$ is X;
X is the moiety

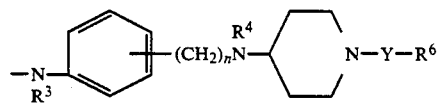

wherein
$R^3$ is hydrogen or lower alkyl;
$R^4$ is hydrogen or

$R^5$ is hydrogen, lower alkyl, phenyl, phenyllower-alkyl or perfluoroloweralkyl;
Y is CO or a bond;
$R^6$ is lower alkyl, cycloloweralkyl, arylalkyl, $—(CH_2)_m$-cycloloweralkyl,

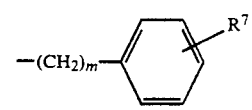

or $—(CH_2)_oCONR^8R^9$ or, in the case when Y is CO, $R^6$ is phenyl;

$R^7$ is hydrogen or

$R^8$ and $R^9$ are, independently, hydrogen, lower alkyl, cycloloweralkyl or $R^8$ and $R^9$ together with the nitrogen atom to which they are attached form a 5–8 membered saturated monoazacyclic ring;
m is 1–3;
n is 1–3;
o is 1–10;
and the pharmacologically acceptable salts thereof.

The more preferred compounds are those having the formula

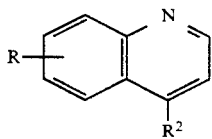

wherein

R is hydrogen, halo or trifluoromethyl;
$R^2$ is the moiety

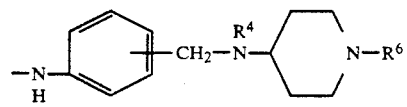

wherein
$R^4$ is hydrogen or

$R^5$ is hydrogen, alkyl of 1 to 16 carbon atoms, phenyl, phenylloweralkyl or perfluoroloweralkyl;
$R^6$ is lower alkyl, cycloloweralkyl, arylalkyl, —$(CH_2)_m$-cycloloweralkyl

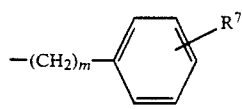

or —$(CH_2)_o CONR^8 R^9$
$R^7$ is hydrogen or

$R^8$ and $R^9$ are, independently, hydrogen, lower alkyl, cycloloweralkyl or $R^8$ and $R^9$ together with the nitrogen atom to which they are attached form a 5-8 membered saturated monoazacyclic ring;

m is 1-3;
o is 1-10;
and the pharmacologically acceptable salts thereof.

The term "lower alkyl", when used alone or in combination, refers to moieties having 1-6 carbon atoms in the carbon chain. The term "aryl," when used alone or in combination, refers to aromatic systems having 6-10 carbon atoms. The term "halo" refers to fluoro, chloro, bromo or iodo. Where —$NR^8R^9$ represents a 5-8 membered, saturated monoazacyclic ring, this refers to moieties such as pyrrolidine, piperidine, hexahydroazepine and octamethyleneimine.

The compounds of the invention, by virtue of having a basic nitrogen, are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like.

The compounds of the invention can be prepared by several basic sequences. According to one such sequence a 2- or 4-haloquinoline is reacted with, for example, methyl 4-aminobenzoate to yield a benzoic acid methyl ester intermediate:

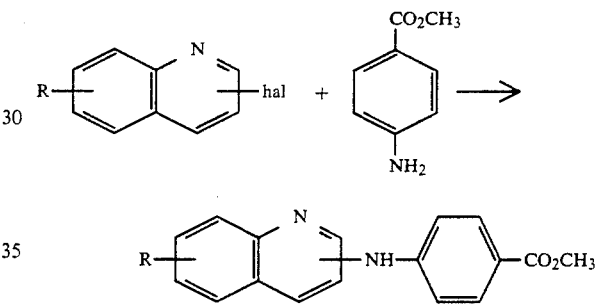

The ester intermediate is saponified to yield a free benzoic acid intermediate, which in turn is reacted with a halogenating agent, such as thionyl chloride, followed by reaction with an appropriately substituted 4-aminopiperidine:

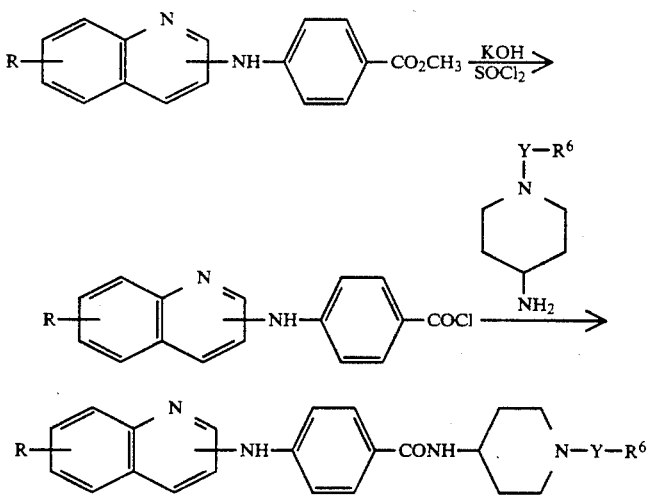

The latter benzamide intermediate is reduced to the desired final product benzenamine using a reducing agent, such as lithium aluminum hydride in tetrahydrofuran.

In a variation of the foregoing sequence, the initial step involves the reaction of 2- or 4-haloquinoline with an aminobenzaldehyde to yield the corresponding amine intermediate:

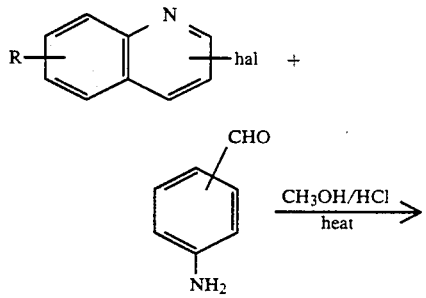

group, the final product amines of the foregoing preparative sequences are reacted with the appropriate acyl chloride or anhydride, optionally in the presence of 4-dimethylaminopyridine as a catalyst, to yield the desired

containing final products:

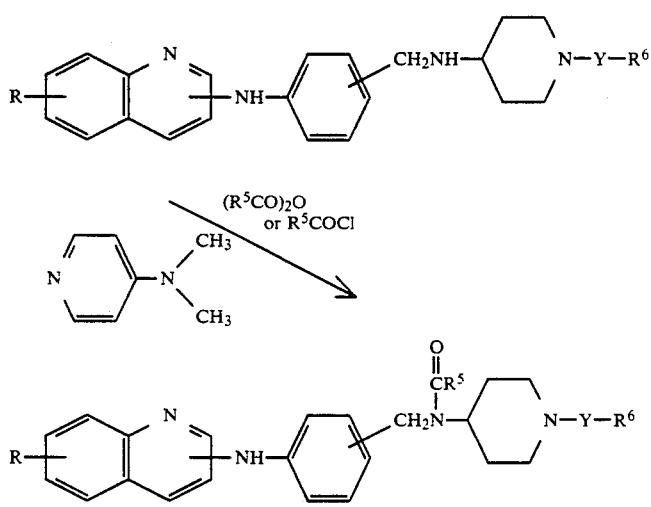

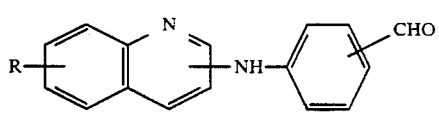

The latter intermediate is then reacted with an appropriately substituted 4-aminopiperidine, followed by reduction to yield the desired final product:

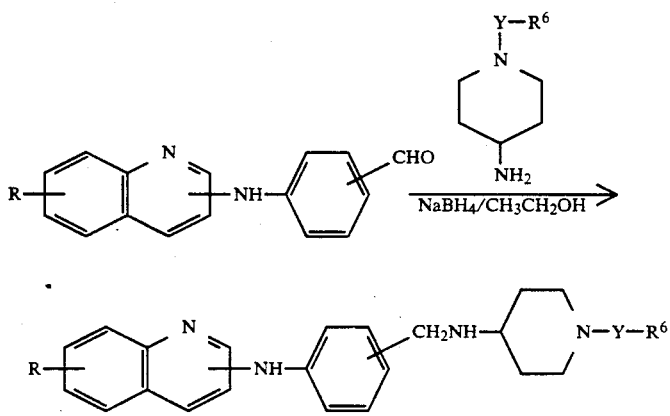

The starting materials for the above-outlined reaction sequences are either commercially available or can be prepared by conventional synthetic procedures. The substituted 4-aminopiperidine starting materials used in the above sequences can be prepared as follows:

When it is desired to prepare the compounds of the invention in which $R^4$ is a

where the 4-piperidone precursor wherein Y is a bond can be prepared according to the procedure reported in U.S. Pat. No. 4,816,464 and in Example 9. When Y is a bond, $R^6$ is

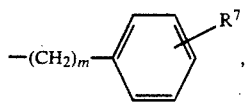

$R^7$ is

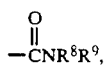

and $R^8$ and $R^9$ are joined together to form a 5- to 8-membered saturated monoazacyclic ring, the compounds can be prepared by the methodology of Example 9, steps A–D wherein the diethylamine in step A is replaced by a cyclic amine

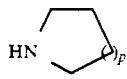

in which p is 1–4. When Y is CO, the substituted 4-aminopiperidine can be prepared by treating dioxa-8-azaspiro[4.5]-decane with an acid chloride followed by hydrolysis of the ketal, according to the procedure for Example 9, step C, to the ketone:

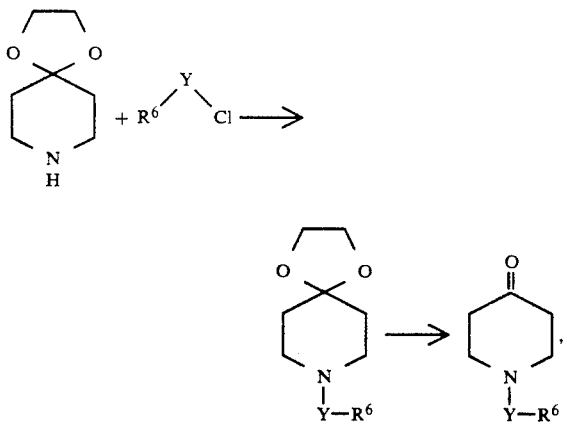

and the resulting ketone is then converted to the 4-aminopiperidine starting materials by the procedure of Example 15, step A or Example 9, step D.

The compounds of the invention, by virtue of their ability to antagonize bradykinin, are analgesic agents, and so are useful in the treatment of and management of pain.

When the compounds of the invention are employed as analgesics, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day.

The bradykinin antagonist effects of the compounds of the invention may be demonstrated by standard pharmacological procedures, which are described more fully in the examples given hereinafter.

These procedures illustrate the ability of the compounds of the invention to bind to bradykinin receptor sites and the ability of the compounds to inhibit the writhing response induced in mice by the exogenous administration of bradykinin.

The following examples show the preparation and pharmacological testing of compounds within the invention.

EXAMPLE 1

N-[4-[[(1-Butyl-4-piperidinyl)amino]methyl]phenyl]-7-chloro-4-quinolinamine

A) 4-[(7-Chloro-4-quinolinyl)amino]benzoic acid methyl ester hydrochloride 4,7-Dichloroquinoline (19.8 g, 100 mmol) and methyl 4-aminobenzoate (15.1 g, 100 mmol) are stirred in 150 mL of methanol in a 500 mL Erlenmeyer flask and heated on a hot plate. After ~15 minutes, a yellow solid precipitates out of solution. Another 100 mL of methanol are added and the large chunks of material are broken up. After another 15 minutes of heating, the flask is allowed to cool for 5 minutes and the product is filtered and washed with ether. Air drying in the funnel overnight affords 26.01 g (74.5 mmol, 75% yield) of compound as a pale-yellow solid: $^1$H NMR (Me$_2$SO-d$_6$, 300 MHz) δ8.74 (d, J=9.3 Hz, 1H), 8.63 (d, J=6.9 Hz, 1H), 8.11 (d, J=8.7 Hz, 2H), 8.09 (d, J=2.1 Hz, 1H), 7.9 (d of d, 1H), 7.62 (d, J=8.4 Hz, 2H), 7.1 (d, 1H), 3.87 (s, 3H).

B) 4-[(7-Chloro-4-quinolinyl)amino]benzoic acid

4-[(7-Chloro-4-quinolinyl)amino]benzoic acid methyl ester hydrochloride (15.0 g, 43.0 mmol) is stirred in 150 mL of 1N KOH (aq) and refluxed for 1.5 hours, over which time the material dissolves. The hot solution is then poured into a 1 L Erlenmeyer flask containing a stirring solution of 107 mL of 1N HCl (aq) in 500 mL of water. A yellow solid forms immediately and the mixture is allowed to cool to room temperature. The solid is filtered and washed with cold methanol and ether, and allowed to air dry in the funnel, to afford 9.31 g (31.2 mmol, 73% yield) of product as a pale yellow solid: $^1$H NMR (Me$_2$SO-d$_6$, 300 MHz) δ12.6 (br s, 1H) 9.4 (br s, 1H), 8.58 (d, J=5.4 Hz, 1H), 8.40 (d, J=9.0 Hz, 1H), 7.94 (m, 3H), 7.6 (d of d, J=2.1, 9.3 Hz, 1H), 7.4 (d, J=8.7 Hz, 2H) 7.2 (d, J=5.6 Hz, 1H).

C) N-(1-Butyl-4-piperidinyl)-4-[(7-chloro-4-quinolinyl)amino]benzamide

4-[(7-Chloro-4-quinolinyl)amino]benzoic acid (4.64 g, 15.5 mmol) is refluxed in 70 mL of thionyl chloride under nitrogen for 4 hours, then allowed to stir at room temperature overnight. The volatiles are removed on a rotary evaporator and two 60 mL portions of benzene are added and the mixture reconcentrated. The resulting yellow solid is then added, in portions, to a rapidly stirring mixture of 1-butyl-4-amino-piperidine bishydrochloride (15.5 mmol, 3.553 g, prepared as described in U.S. Pat. No. 3,875,165) and Na$_2$CO$_3$ (160 mmol, 16.96 g) in 60 mL of water and 75 mL of chloroform at 0° C. After the addition, the reaction mixture is warmed to room temperature and stirred overnight. The solid is then filtered and boiled in 250 mL of ethanol. The mixture is filtered hot and the filtrate is concentrated under reduced pressure, affording a yellow solid which is dried in vacuo at 60° C. overnight. This affords 4.95 g (11.3 mmol, 73% yield) of yellow solid: $^1$H NMR (Me$_2$SO-d$_6$, 400 MHz) δ9.3 (s, 1H), 8.5 (d, J=5.6 Hz, 1H), 8.4 (d, J=8.9 Hz, 1H), 8.1 (d, J=8.1 Hz, 1H), 7.9 (d, J=2.1 Hz, 1H), 7.9 (d, J=8.7 Hz, 2H), 7.6 (d of d, J=2.2, 9.0 Hz, 1H), 7.4 (d, J=8.3 Hz, 2H), 7.1 (d, J=5.4 Hz, 1H), 3.7 (br m, 1H), 2.8 (m, 2H), 2.2 (br t, J=7.4 Hz, 2H), 1.9 (m, 2H), 1.7-1.8 (m, 2H), 1.5-1.6 (m, 2H), 1.3-1.4 (m, 2H), 1.2-1.3 (m, 2H), 0.86 (t, J=7.3 Hz, 3H).

D) N-[4-[[(1-Butyl-4-piperidinyl)amino]methyl]phenyl]-7-chloro-4-quinolinamine N-(1-Butyl-4-piperidinyl)-4-[(7-chloro-4-quinolinyl)amino]benzamide (2.5 g, 5.7 mmol) is added in small portions to a mixture of lithium aluminum hydride (17.16 mmol, 651 mg) in 25 mL of tetrahydrofuran at 0° C. under nitrogen. After the addition, the reaction mixture is allowed to warm to room temperature and stirred for three days. It is quenched by the slow addition of 0.9 mL of water, 0.9 mL of 2.5N NaOH and 2.7 mL of water. Five mL of tetrahydrofuran are added and the mixture is filtered through Celite. The solid is boiled three times in tetrahydrofuran and refiltered. The pooled filtrates are then concentrated in vacuo to a yellow foam. Flash chromatography on silica gel (50 mm column, 12% ammonia saturated methanol in methylene chloride eluent) affords 1.155 g (2.73 mmol, 48% yield) of product which is recrystallized from 20 mL of toluene. This results in 0.51 g of product which is dried in vacuo for two days: mp 143°–146° C.; IR (KBr) 3350, 2930, 2800, 1615, 1570 cm$^{-1}$; $^1$H NMR (CDCl$_3$ 400 MHz) δ8.5 (d, J=5.3 Hz, 1H), 8.0 (d, J=2.1 Hz, 1H), 7.9 (d, J=9.0 Hz, 1H), 7.5 (d of d, J=2.2, 9.0 Hz, 1H), 7.4 (d, J=8.3 Hz, 2H), 7.2 (d, J=8.4 Hz, 2H), 6.9 (d, J=5.3 Hz, 1H), 6.6 (s, 1H), 3.8 (s, 2H), 2.9-3.0 (m, 2H), 2.5-2.6 (m, 1H), 2.3-2.4 (m, 2H), 1.9-2.1 (m, 4H), 1.4-1.6 (M, 4H), 1.3-1.4 (m, 2H), 0.9 (t, J=7.3 Hz, 3H), MS (EI), m/z (rel intensity)=422 (M$^+$, 40), 282 (74), 267 (100); Karl Fisher, 3.17% H$_2$O;

Analysis for: C$_{25}$H$_{31}$ClN$_4$. 0.75 H$_2$O: Calculated: C, 68.80; H, 7.50; N, 12.84. Found: C, 69.01; H, 7.38; N, 12.81.

EXAMPLE 2

N-(1-Butyl-4-piperidinyl)-N-[[4-[(7-chloro-4-quinolinyl)amino]phenyl]methyl]acetamide N-[4-[[(1-Butyl-4-piperidinyl)amino]methyl]phenyl]-7-chloro-4-quinolinamine (281 mg, 0.66 mmol) of Example 1 is stirred in 4.5 mL of tetrahydrofuran at room temperature under nitrogen and treated with acetic anhydride (0.66 mmol, 67 mg, 62 μL). After 53 minutes, another 30 μL of acetic anhydride is added and the reaction mixture is stirred an additional ten minutes. It is then concentrated in vacuo and purified by flash chromatography on silica gel (30 mm column, 8% ammonia saturated methanol in methylene chloride eluent), affording 261 mg (0.561 mmol, 85% yield) of product as an amorphous solid: mp 80°–110° C.; IR (KBr) 3300, 2940, 1630, 1570 cm$^{-1}$; $^1$H NMR (Me$_2$SO-d$_6$, 400 MHz, mixture of rotamers) δ9.08 (s, 0.5H), 9.03 (s, 0.5H), 8.4 (m, 2.5H), 7.87 (m, 0.5H), 7.56 (m, 1H), 7.3 (d, J=8.4 Hz, 1H), 7.2-7.3 (m, 3H), 6.9 (d, J=5.3 Hz, 0.5H), 6.8 (d, J=5.3 Hz, 0.5 Hz), 4.54 (s, 1H), 4.48 (s, 1H), 4.2-4.3 (m, 0.5H), 3.6-3.7 (m, 0.5H), 2.8-2.9 (m, 2H), 2.2 (m, 3.5H), 1.97 (s, 1.5H), 1.9-1.2 (m, 10H), 0.8 (m, 3H); MS (EI), m/z (rel intensity)=464 (M$^+$, 30), 267 (100); Karl Fisher, 1.32% H$_2$O;

Analysis for: C$_{27}$H$_{33}$ClN$_4$O. 0.35 H$_2$O: Calculated: C, 68.81; H, 7.21; N, 11.89. Found: C, 68.90; H, 7.11; N, 11.79.

EXAMPLE 3

N-(1-Butyl-4-piperidinyl)-N-[[4-(4-quinolinylamino)phenyl]methyl]acetamide

N-(1-Butyl-4-piperidinyl)-N-[[4-(4-quinolinylamino)phenyl]methyl]acetamide can be prepared as described in Example 2 by substituting 4-chloroquinoline for 4,7-dichloroquinoline as the starting material in Example 1: mp 85°–105° C.; IR (KBr) 3600, 3400, 2960, 2920, 1635 cm$^{-1}$; $^1$H NMR (Me$_2$SO-d$_6$, 400 MHz, mixture of rotamers) δ8.93 (s, 0.5H), 8.89 (s, 0.5H), 8.3-8.5 (m, 2H), 7.85 (m, 1H), 7.68 (m, 1H), 7.5 (m, 1H), 7.2-7.4 (m, 4H), 6.9 (d, J=5.2 Hz, 0.5H), 6.8 (d, J=5.2 Hz, 0.5 Hz), 4.54 (s, 1H), 4.48 (s, 1H), 4.27 (m, 0.5H), 3.68 (m, 0.5H), 2.8 (m, 2H), 2.2 (m, 3.5H), 1.98 (s, 1.5H), 1.8-2.0 (m, 2H), 1.2-1.7 (m, 10H), 0.84 (m, 3H); MS (EI), m/z (rel intensity)=430 (M$^+$, 38), 290 (38), 233 (100); Karl Fisher, 1.43% H$_2$O;

Analysis for: C$_{27}$H$_{34}$N$_4$O. 0.35 H$_2$O: Calculated: C, 74.23; H, 8.00; N, 12.82. Found: C, 73.89; H, 7.86; N, 12.82.

EXAMPLE 4

N-(1-Butyl-4-piperidinyl)-N-[[4-[7-chloro-4-quinolinyl)amino]phenyl]methyl]benzamide, hydrochloride N-(1-Butyl-4-piperidinyl)-N-[[4-[7-chloro-4-quinolinyl)amino]phenyl]methyl]benzamide hydrochloride can be prepared as a hygroscopic material as described in Example 2 by using benzoic anhydride in place of acetic anhydride and by adding 2-4 equivalents of triethylamine and a catalytic amount of 4-dimethylaminopyridine to the reaction mixture: mp 208°-216° C.; IR (KBr) 3430, 2940, 1620 cm$^{-1}$; $^1$H NMR (Me$_2$SO-d$_6$, 400 MHz) δ8.8 (d, J=9.0 Hz, 1H), 8.5 (d, J=6.7 Hz, 1H), 8.1 (d, J=2.0 Hz, 1H), 7.8 (d, J=8.3 Hz, 1H), 7.2-7.6 (m, 9H), 6.8 (d, J=6.5 Hz, 1H), 1.2-4.8 (m, 17H), 0.86 (m, 3H); MS (FAB), m/z (rel intensity)=(M+, 60), 267 (100); Karl Fisher, 5.72% H$_2$O;

Analysis for: C$_{32}$H$_{35}$ClN$_4$O. 1.85 H$_2$O.HCl: Calculated: C, 64.39; H, 6.70; N, 9.39. Found: C, 62.66; H, 6.43; N, 9.11.

EXAMPLE 5

N-(1-Butyl-4-piperidinyl)-N-[[4-[(7-chloro-4-quinolinyl)amino]phenyl]methyl]benzenepropanamide, hydrochloride N-[4-[[(1-Butyl-4-piperidinyl)amino]methyl]phenyl]-7-chloro-4-quinolinamine (0.50 g, 1.18 mmol) of Example 1 was stirred in 5 ml of tetrahydrofuran at 0° C. and treated with 0.25 mL (1.77 mmol) of triethylamine followed by hydrocinnamoyl chloride (0.176 mL, 1.18 mmol). The reaction mixture is allowed to warm to room temperature and stirred overnight. If starting material is still present as determined by TLC analysis, an additional 0.05 mL of hydrocinnamoyl chloride are added. The completed reaction is concentrated in vacuo. Flash chromatography on silica gel (40 mm column, 5% ammonia saturated methanol in methylene chloride eluent) affords 0.582 g (1.05 mmol, 89% yield) of product. The hydrochloride salt is prepared by dissolving 1.02 mmol of the free base in 5 mL of methanol and treating the solution with 1.02 mL of 1N HCl in methanol. The solution is boiled and treated with ether until cloudy. Cooling results in an oil, which is triturated with ether for four days. This results in a hygroscopic yellow solid which is dried in vacuo overnight: mp 157°-160° C., IR (KBr) 3400, 2010, 1630, 1610 cm$^{-1}$; $^1$H NMR (Me$_2$SO-d$_6$, 400 MHz, mixture of rotamers) δ9.3 (m, 1H), 8.5 (m, 2H), 7.9 (d,j=2.2 Hz, 1H), 7.6 (m, 1H), 7.1-7.3 (m, 9H), 6.8 (m, 1H), 1.2-4.6 (m, 21H), 0.8 (m, 3H); MS (CI+), m/z (rel intensity)=555 (M+,38), 416 (32), 289 (100); Karl Fisher, 4.02% H$_2$O);

Analysis for: C$_{34}$H$_{39}$ClN$_4$O.HCl.1.36H$_2$O; Calculated: C, 66.28; H, 6.99; N, 9.09. Found: C, 65.87; H, 6.69; N, 8.95.

EXAMPLE 6

N-(1-Butyl-4-piperidinyl)-N-[[4-[(7-chloro-4-quinolinyl)amino]phenyl]-methyl]-2,2,3,3,4,4,4-heptafluorobutanamide, hydrochloride N-(1-Butyl-4-piperidinyl)-N-[[4-[(7-chloro-4-quinolinyl)amino]-phenyl]methyl]-2,2,3,3,4,4,4-heptafluorobutanamide hydrochloride can be prepared as a hygroscopic material as described in Example 1 by substituting perfluorobutyric anhydride for acetic anhydride and by adding 2-4 equivalents of triethylamine and a catalytic amount of 4-dimethylaminopyridine to the reaction mixture; mp 192°-195° C.; IR (KBr) 3400, 2940, 1670 cm$^{-1}$;$^1$H NMR (Me$_2$SO-d$_6$, 400 MHz, mixture of rotamers) δ9.6-10.4 (br m, 2H), 8.5-8.6 (m, 2H), 8.0 (s, 1H), 7.7 (m, 1H), 7.3-7.5 (m, 4H), 6.8-6.9 (m, 1H), 1.2-4.8 (m, 17H), 0.9 (m, 3H); MS (CI+), m/z (rel intensity)=619 (M+,11), 353 (40), 246 (50); Karl Fisher, 2.88% H$_2$O;

Analysis for: C$_{29}$H$_{30}$ClF$_7$N$_4$O.HCl.1.08 H$_2$O; Calculated: C, 51.61; H, 4.95; N, 8.30. Found: C, 49.33; H, 4.16; N, 7.63.

EXAMPLE 7

N-(1-butyl-4-piperidinyl)-N-[[4-[(7-chloro-4-quinolinyl)amino]-phenyl]methyl]-2,2,2-trifluoroacetamide, hydrochloride N(1-Butyl-4-piperidinyl)-N-[[4-[(7-chloro-4-quinolinyl)amino[-phenyl]methyl]-2,2,2-trifluoroacetamide hydrochloride can be prepared as a hygroscopic material as described in Example 2 by substituting trifluoroacetic anhydride for acetic anhydride and by adding 2-4 equivalents of triethylamine and a catalytic amount of 4-dimethylaminopyridine to the reaction mixture: mp 174°-176° C.; IR (KBr) 3400, 2949, 1680 cm$^{-1}$;$^1$H NMR (Me$_2$SO-d$_6$, 400 MHz, mixture of rotamers) δ9.5 (br s, 1H), 8.4-8.5 (m, 2H), 7.9 (d,J=2.3 Hz, 1H), 7.6 (m, 1H), 7.2-7.4 (m, 4H), 6.9 (m, 1H), 1.4-4.8 (m, 17H), 0.9 (m, 3H); MS (CI+), m/z (rel intensity)=519 (M+, 100), 269 (38), 253 (66); Karl Fisher, 4.00% H$_2$O;

Analysis for: C$_{27}$H$_{30}$F$_3$ClN$_4$O.HCl.1.27 H$_2$O; Calculated: C, 56.07; H, 5.85; N, 9.69. Found: C, 55.31; H, 5.28; N, 9.15.

EXAMPLE 8

N-(1-Butyl-4-piperidinyl)-N-[[4-[(7-chloro-4-quinolinyl)-amino]phenyl]methyl]butanamide, hydrochloride N-(1-Butyl-4-piperidinyl)-N-[[4[(7-chloro-4-quinolinyl)amino]-phenyl]methyl]butanamide hydrochloride can be prepared as a hygroscopic material as described in Example 2 by substituting butyric anhydride for acetic anhydride and by adding 2-4 equivalents of triethylamine and a catalytic amount of 4-dimethylaminopyridine to the reaction mixture: mp 151°-155° C.; IR (KBr) 3400, 3200, 2940, 1625, 1605 cm$^{-1}$; $^1$H NMR (Me$_2$SO-d$_6$, 400 MHz, mixture of rotamers) δ9.2 (br s, 1H), 8.4-8.5 (m, 2H), 7.9 (s, 1H), 7.6 (d, J=8.9 Hz, 1H), 7.2-7.4 (m, 4H), 6.8-6.9 (m, 1H), 1.2-4.6 (m, 21H), 0.8-1.0 (m, 6H); MS (CI+), m/z (rel intensity)=493 (M+, 100), 459 (17), 354 (36); Karl Fisher, 4.58% H$_2$O;

Analysis for: C$_{29}$H$_{37}$ClN$_4$O.HCl.1.39 H$_2$O; Calculated: C, 62.81; H, 7.41; N, 10.10. Found: C, 63.45; H, 7.06; N, 9.80.

EXAMPLE 9

4-[[4-[[[4-[(7-Chloro-4-quinolinyl)amino]phenyl]methyl]amino]-1-piperidinyl]methyl]-N,N-diethylbenzamide, hydrochloride A) 4-(Bromomethyl)-N,N-diethylbenzamide 4-Bromomethylbenzoic acid (50 g, 233 mmol) is dissolved in 500 mL of tetrahydrofuran containing a few drops if N,N-dimethylformamide at room temperature under nitrogen and treated dropwise over 1 hour with oxalyl chloride (268 mmol, 34.0 g, 23.4 mL). After the addition, the reaction mixture is stirred for 0.5 hour, at which point the solvent is removed in vacuo. The solid residue is dissolved in 200 mL of tetrahydrofuran and poured into a rapidly stirring solution of diethylamine (536 mmol, 39.2 g, 55.7 mL) in 400 mL of water. After the mixture cools to room temperature, 100 mL of ether are added and the two phases are separated. The organic phase is dried over magnesium sulfate and concentrated in vacuo affording 54.01 g (200 mmol, 86% yield) of the product as a white solid.

B) 4-(1,4-Dioxa-8-azaspiro[4.5]dec-8-ylmethyl)-N,N-diethylbenzamide 1,4-Dioxa-8-azaspiro[4.5]-decane (200 mmol, 28.6 g, 25.6 mL) is dissolved in 160 ml of dry acetonitrile under nitrogen and treated with $K_2CO_3$ (220 mmol, 30.3 g) followed by dropwise addition over 1.5 hours of 4-(bromomethyl)-N,N-diethylbenzamide (200 mmol, 54.01 g) as a solution in 81 mL of acetonitrile. After 16 hours, the reaction mixture is poured into 250 mL of water and extracted twice with 150 mL of methylene chloride. The pooled extracts were washed with 250 mL of brine, dried over $Na_2SO_4$ and concentrated in vacuo affording 63.9 g (192 mmol, 96% yield) of the product as a yellow-orange oil.

C) N,N-Diethyl-4-[(4-oxo-1-piperidinyl)methyl]benzamide 4-(1,4-Dioxa-8-azaspiro[4.5]dec-8-ylmethyl)-N,N-diethylbenzamide (63.9 g, 192 mmol) is dissolved in 193 mL of tetrahydrofuran and treated with a solution of concentrated sulfuric acid (77 mL) in water (309 mL). The solution is allowed to stir for three days and then refluxed for 17 hours. It is neutralized with 2.5N NaOH and extracted with 400 mL, 200 mL and then 100 of methylene chloride. The pooled extracts are dried over $Na_2SO_4$ and concentrated in vacuo affording 58.74 g (193 mmol, 100% yield) of product as a yellow oil: IR (thin film) 3500, 2980, 2810, 1720, 1630 cm$^{-1}$; $^1$H NMR (Me$_2$SO-d$_6$, 400 MHz) δ7.4 (d,J=8.1 Hz, 2H), 7.3 (d,J=8.2 Hz, 2H), 3-3.6 (m, 8H), 2.68 (t,J=6.1 Hz, 2H), 2.34 (t,J=6.0 Hz, 2H), 1.1 (m, 6H).

D) 4-[(4-Amino-1-piperidinyl)methyl]-N,N-diethylbenzamide

N,N-Diethyl-4-[(4-oxo-1-piperidinyl)methyl]benzamide (58.74 g, 193 mmol) is dissolved in 580 mL of ethanol and treated with 290 mL of 30% NaOH followed by hydroxylamine hydrochloride (26.82 g, 386 mmol). The mixture is refluxed for 45 minutes, the heating mantle removed and the reaction mixture stirred with an overhead stirrer as 38.4 g of 50/50 aluminum-nickel alloy (powder) are added in small portions with ice cooling. After the addition, the mixture is refluxed for 1.75 hours, then allowed to stand at room temperature overnight, filtered through Solka Floc and most of the ethanol is evaporated in vacuo from the filtrate. The resulting aqueous phase is extracted with 3×100 mL of ether. The pooled extracts are concentrated in vacuo and the oily residue is poured into 500 mL of brine and continuously extracted with ether overnight. Concentration of the extract affords 37 g of product which is purified by flash chromatography on silica gel (110 mm column, 5% ammonia saturated methanol in methylene chloride eluent) affording 7.08 g (24.4 mmol, 13% yield) of product: $^1$H NMR (Me$_2$SO-d$_6$, 300 MHz) δ7.33 (d,J=8.2 Hz, 2H), 7.27 (d,J=8.2 Hz, 2H), 1.0-3.5 (m, 21H).

E) 4-[(7-Chloro-4-quinolinyl)amino]benzaldehyde, hydrochloride 4,7-Dichloroquinoline (50 g, 252 mmol) and 4-aminobenzaldehyde (30.6 g, 252 mmol) are stirred in 300 mL of methanol and treated with 126 mL of 2 N HCl. The mixture is boiled on a hot plate and after ∼15 minutes, a thick yellow precipitate forms. The heating is continued at a low setting for 3 hours at which point the mixture is allowed to cool to room temperature. The yellow solid is filtered, washed with cold methanol, then ether and dried in vacuo at 60° C. for three days affording 64.65 g (203 mmol, 80% yield) of product: $^1$H NMR (Me$_2$SO-d$_6$, 300 MHz) δ11.4 (br s, 1H), 10.06 (s, 1H), 8.95 (d,J=9.2 Hz, 1H), 8.65 (d,J=6.9 Hz, 1H), 8.24 (d,J=2.1 Hz, 1H), 8.09 (d,J=8.5 Hz, 2H), 7.92 (d of d,J=2.0, 9.2 Hz, 1H), 7.76 (d,J=8.5 Hz, 2H), 7.13 (d,J=7.0 Hz, 1H).

F) 4-[[4-[[[4-[(7-Chloro-4-quinolinyl)amino]phenyl]methyl]amino]-1-piperidinyl]-methyl]-N,N-diethylbenzamide, hydrochloride 4-[(4-Amino-1-piperidinyl)methyl]-N,N-diethylbenzamide (3.81 g, 13.16 mmol) and 4-[(7-chloro-4-quinolinyl)amino]benzaldehyde hydrochloride (13.16 mmol, 4.20 g) are refluxed for 28 hours in 52 mL of toluene under nitrogen with azeotropic removal of water. The toluene is poured off the thick oil, which is then rinsed once with fresh toluene. The remaining traces of solvent are removed in vacuo and the resulting gum is dissolved in 55 mL of ethanol and treated with NaBH$_4$ (14.6 mmol, 552 mg). The reaction mixture is refluxed for 50 minutes, treated with another 200 mg of NaBH$_4$ and refluxed an additional 10 minutes. The reaction mixture is poured over 100 mL of ice, which results in the formation of an orange oil. After stirring rapidly for seven days, the water is decanted and the oil is purified by flash chromatography on silica gel (65 mm column, 5% ammonia saturated methanol in methylene chloride eluent) which affords 1.55 g (2.79 mmol, 21% yield) of the title compound as the free base. Of this, 0.95 g (1.7 mmol) are dissolved in 5 mL of methanol and treated with 1.7 mL of 1N ethereal HCl. The resulting solution is concentrated in vacuo and the residue is triturated with ether for 23 hours. The resulting yellow powder is filtered, washed with ether and dried in vacuo at 60° C. for 16.5 hours, affording 896 mg of the title compound: mp 166°-190° C. (softens slowly over this range); $^1$H NMR (Me$_2$SO-d$_6$, 400 MHz) δ9.37 (br s, 1H), 8.5 (m, 2H), 7.91 (d,J=2.2 Hz, 1H), 7.6 (m, 3H), 7.28-7.42 (m, 6H), 6.96 (d,J=5.4 Hz, 1H), 4.12 (s, 2H), 2.9-3.6 (m, 10H), 2.1 (m, 4H), 1.7-1.8 (m, 2H), 1-1.2 (m, 6H);

Analysis for: $C_{33}H_{38}ClN_5O \cdot HCl$: Calculated: C, 66.88; H, 6.63; N, 11.82. Found: C, 66.72; H, 6.25; N, 11.75.

EXAMPLE 10

7-Chloro-N-[4-[[[1-(phenylmethyl)-4-piperidinyl]amino]methyl]phenyl]-4-quinolinamine 7-Chloro-N-[4-[[[1-(phenylmethyl)-4-piperidinyl]amino]methyl]phenyl]-4-quinolinamine can be prepared by the procedure of Example 9 by substituting, in step F, 4-amino-1-benzylpiperidine for 4-[(4-amino-1-piperidinyl)methyl]-N,N-diethylbenzamide: mp 160.5°–163.5° C.; IR (KBr) 3440, 2930, 2800, 1610, 1580 cm$^{-1}$; $^1$H NMR (Me$_2$SO-d$_6$, 400 MHz) δ9.0 (s, 1H), 8.4 (m, 2H), 7.87 (d, J=2.2 Hz, 1H), 7.54 (dd, J=2.2, 9.0 Hz, 1H), 7.2–7.4 (m, 9H), 6.8 (d, J=5.3 Hz, 1H) 3.7 (s, 2H), 3.4 (s, 2H), 2.7 (m, 2H), 2.4 (m, 1H), 1.8–2 (m, 4H), 1.3 (m, 2H); MS (+FAB), m/z (rel intensity)=457 (19), 267 (39).

Analysis for: C$_{28}$H$_{29}$ClN$_4$: Calculated: C, 73.59; H, 6.40; N, 12.26. Found: C, 73.74; H, 6.64; N, 12.20.

EXAMPLE 11

N-[[4-[(7-Chloro-4-quinolinyl)amino]phenyl]methyl]-N-[1-(phenylmethyl)-4-piperidinyl]butanamide, hydrochloride, 0.57 hydrate N-[[4-[(7-Chloro-4-quinolinyl)amino]phenyl]methyl]-N-[1-(phenylmethyl)-4-piperidinyl]butanamide can be prepared from Example 10 by the procedure of Example 2 by substituting butyric anhydride for acetic anhydride. The hydrochloride salt is prepared by dissolving 541 mg of the free base in 5 ml of methanol, treating with 1.03 ml of 1N HCl in ether and solvent removal under reduced pressure. The residue is then triturated in ether overnight affording 455 mg of the hydrochloride: mp 156°–162° C.; IR (KBr) 3420, 2950, 1630, 1610 cm$^{-1}$; $^1$H NMR (Me$_2$SO-d$_6$, 400 MHz, mixture of rotamers) δ9.7 (br s, 1H), 8.4–8.5 (m, 2H), 7.95 (s, 1H), 7.2–7.6 (m, 11H); 6.8–6.9 (m, 1H), 1.4–4.6 (m, 17H), 0.92 (t, J=7.3 Hz, 1.5H, rotamer a), 0.8 (t, J=7.3 Hz, 1.5H, rotamer b); MS (CI+), m/z (rel intensity)=527 (M+H, 6), 429 (100), 369 (90); Karl Fisher, 1.76% H$_2$O.

Analysis for: C$_{32}$H$_{35}$ClN$_4$O.HCl 0.5 H$_2$O: Calculated: C, 66.98; H, 6.52; N, 9.76. Found: C, 67.17; H, 6.29; N, 9.85.

EXAMPLE 12

4-[[4-[[[4-[(7-Chloro-4-quinolinyl)amino]phenyl]methyl]-(1-oxobutyl)amino]-1-piperidinyl]methyl]-N,N-diethylbenzamide, hydrochloride, 0.76 hydrate The title compound can be prepared from the free base of Example 9 by the procedure of Example 2 by substituting butyric anhydride for acetic anhydride. The hydrochloride salt is prepared by dissolving 520 mg of the free base in 5 ml of methanol, treating with 0.83 ml of 1N HCl in ether and solvent removal under reduced pressure. The residue is then triturated in ether overnight affording 432 mg of the hydrochloride: mp 157°–162° C.; IR (KBr) 3420, 2960, 2930, 1630 cm$^{-1}$; $^1$H NMR (Me$_2$SO-d$_6$, 400 MHz, mixture of rotamers) δ9.8–10 (br s, 1H), 8.6 (m, 1H), 8.45 (m, 1H), 7.8 (s, 1H), 7.2–7.7 (m, 10H), 6.8 (m, 1H), 4.5–4.6 (m, 2H), 4.1 (br s, 2H), 1.4–3.4 (m, 17H), 1–1.2 (m, 6H), 0.92 (t, J=7.3 Hz, 1.5H, rotamer a), 0.80 (t, J=7.4 Hz, 1.5H, rotamer b); MS (+FAB), m/z (rel intensity)=626 (M+H, 49), 267 (100); Karl Fisher, 2.00% H$_2$O.

Analysis for: C$_{37}$H$_{44}$ClN$_5$O$_2$.HCl.0.76 H$_2$O: Calculated: C, 65.71; H, 6.93; N, 10.35. Found: C, 65.90; H, 6.74; N, 10.53.

EXAMPLE 13

4-[[[4-[(7-Chloro-4-quinolinyl)amino]phenyl]methyl]amino]-N,N-diethyl-1-piperidinehexanamide, tris(trifluoroacetate), 0.42 hydrate A) 6-Bromo-N,N-diethylhexanamide A solution of 6-bromohexanoyl chloride (100 g, 468 mmol) in 350 ml of tetrahydrofuran was poured into a solution of diethylamine (1.08 moles, 79 g, 112 ml) in 800 ml of rapidly stirring water. The mixture was then extracted with 2×200 ml of CH$_2$Cl$_2$ and the pooled extracts were washed with 250 ml of brine. Drying over Na$_2$SO$_4$ and concentration under reduced pressure afforded 111.6 g (446 mmol, 100% yield) of product as a pale yellow oil: $^1$H NMR (Me$_2$SO-d$_6$, 300 MHz) δ3.5 (t, J=6.7 Hz, 2H), 3.2–3.3 (m, 4H), 2.3 (t, J=7.5 Hz, 2H), 1.8 (m, 2H), 1.3–1.6 (m, 4H), 1.1 (t, J=7.1 Hz, 3H), 0.99 (t, J=7.0 Hz, 3H).

B) 4-Amino-N,N-diethyl-1-piperidinehexanamide 4-amino-N,N-diethyl-1-piperidinehexanamide can be prepared from 6-bromo-N,N-diethylhexanamide (step A) and 1,4-dioxa-8-azaspiro[4.5]-decane as described in U.S. Pat. Nos. 3,875,165 and 4,816,464.

C)

4-[[[4-[(7-Chloro-4-quinolinyl)amino]phenyl]methyl]amino]-N,N-diethyl-1-piperidinehexanamide tris(trifluoroacetate) 0.42 hydrate The free base of the title compound can be prepared by the procedure of Example 9 by substituting, in step F, 4-amino-N,N-diethyl-1-piperidinehexanamide for 4-[(4-amino-1-piperidinyl)methyl]-N,N-diethylbenzamide. Reverse phase chromatography (C18, 70 m gradient from 0.1% trifluoroacetic acid in 95/5 H$_2$O/MeCN to 0.1% trifluoroacetic acid in 5/95 H$_2$O/MeCN) then affords Example 13: mp 123.5°–128° C.; IR (KBr) 3400, 2950, 1660 cm$^{-1}$; $^1$H NMR (Me$_2$SO-d$_6$, 400 MHz) δ10 97 (s, 1H), 9.8 (br s, 1H), 9.4 (br s, 2H), 8.7 (d, J=9.1 Hz, 1H), 8.6 (d, J=6.8 Hz, 1H), 8.1 (d, J=2.3 Hz, 1H), 7.9 (dd, J=2.1, 9.1 Hz, 1H), 7.7 (d, J=8.5 Hz, 2H), 7.55 (d, J=8.5 Hz, 2H), 6.8 (d, J=6.8 Hz, 1H), 4.3 (br s, 2H), 2.8–4 (m, 11H), 2.2–2.4 (m, 4H), 1.9 (m, 2H), 1.65 (m, 2H), 1.5 (m, 2H), 1.3 (m, 2H), 1.09 (t, J=7.1 Hz, 3H), 0.99 (t, J=7.1 Hz, 3H); MS (+FAB), m/z (rel intensity)=536(M+H, 28), 267 (100); Karl Fisher, 0.85% H$_2$O.

Analysis for: C$_{31}$H$_{42}$N$_5$O$_2$Cl.3 CF$_3$COOH.0.43 H$_2$O: Calculated: C, 49.27; H, 5.12; N, 7.76. Found: C, 49.02, H, 4.76; N, 7.56.

EXAMPLE 14

4-[[[4-[(7-Chloro-4-quinolinyl)amino]phenyl]methyl](1-oxobutyl)amino]-N,N-diethyl-1-piperidinehexanamide, 0.56 hydrate The title compound can be prepared as a hygroscopic material from the free base of Example 13 by the procedure of Example 2 by substituting butyric anhydride for acetic anhydride: mp 55°–70° C. (amorphous); IR (KBr) 3410, 3280, 2920, 1620 cm$^{-1}$, $^1$H NMR (Me$_2$SO-d$_6$, 400 MHz, mixture of rotamers) δ9.1–6.8 (m, 10H), 4.5 (m, 2H), 4.3 (m, 0.5H, rotamer a), 3.7 (m, 0.5H, rotamer b), 1.2–3.4 (m, 26H), 1.1 (t, J=7.0 Hz, 3H), 0.9–1 (m, 4.5H), 0.81 (t, J=7.4 Hz, 1.5H); MS (+FAB), m/z (rel intensity)=606 (M+H, 30), 267 (100); Karl Fisher, 1.62% H$_2$O.

Analysis for: C$_{35}$H$_{48}$ClN$_5$O$_2$.0.56 H$_2$O: Calculated: C, 68.20; H, 8.023; N, 11.36. Found: C, 67.59; H, 7.93; N, 11.19.

EXAMPLE 15

1-Benzoyl-N-[[[4-[(7-chloro-4-quinolinyl)amino]-phenyl]methyl]-4-piperidinanaminetrifluoroacetate (1:2), 1.03 hydrate

A) 4-Amino-1-benzoylpiperidine

N-Benzoyl-4-piperidone (45.92 g, 226 mmol) was converted to the oxime by treatment with $HONH_2.HCl$ (237 mmol, 16.49 g) in 90 ml of methanol and 90.4 ml of 2.5N NaOH. After stirring overnight, the reaction was concentrated under reduced pressure and three times treated with toluene and reconcentrated to remove the last traces of water. The resulting oxime (57 g) was dissolved in 1L of methanol, treated with 226 ml of 1N HCl and 4 g of $PtO_2$. The mixture was then hydrogenated in a Paar apparatus at 50 psi. After 16.75 h, the catalyst was filtered and the methanol was concentrated in vacuo. Water (100 ml) was then added to the aqueous phase that was then extracted with 7×700 ml of $CH_2Cl_2$. The aqueous phase was made basic with 2.5N NaOH and extracted with 5×100 ml of $CH_2Cl_2$. The pooled extracts were concentrated in vacuo affording 18.17 g (88.9 mmol, 39% overall yield) of 4-amino-1-benzoylpiperidine as a yellow oil.

B) 1-Benzoyl-N-[[[4-[(7-chloro-4-quinolinyl)amino]-phenyl]methyl]-4-piperidinanamine trifluoroacetate (1:2) 1.03 hydrate The free base of the title compound can be prepared by the procedure of Example 9 by substituting, in step F, 4-amino-1-benzoylpiperidine for 4-[(4-Amino-1-piperidinyl)methyl]-N,N-diethylbenzamide. Reverse phase chromatography (C18, 70 m gradient from 0.1% trifluoroacetic acid in 95/5 $H_2O$/MeCN to 0.1% trifluoroacetic acid in 5/95 $H_2O$/MeCN) then affords Example 15: mp 213.5°–215.5° C.; IR (KBr) 3420, 3200, 3050, 1670, 1590 cm$^{-1}$; $^1$H NMR (Me$_2$SO-d$_6$, 400 MHz) δ10.94 (br s, 2H), 8.7 (d, J=9.1 Hz, 1H), 8.6 (d, J=6.9 Hz, 1H), 8.1 (d, J=2.1 Hz, 1H), 7.9 (dd, J=2.1, 9.1 Hz, 1H), 7.7 (d, J=8.4 Hz, 2H), 7.5 (d, J=8.4 Hz, 2H), 7.4–7.5 (m, 3H), 7.3–7.4 (m, 2H), 6.8 (d, J=6.9 Hz, 1H), 1.2–4.6 (m, 11H); MS (+FAB), m/z (rel intensity)=471 (M+H, 13), 267 (100); Karl Fisher, 2.58% $H_2O$.

Analysis for: $C_{28}H_{27}ClN_4O.2\ CF_3COOH.1.03\ H_2O$: Calculated: C, 53.56; H, 4.36; N, 7.81. Found: C, 53.88; H, 4.18; N, 7.91.

EXAMPLE 16

4-[[[4-[(7-Chloro-4-quinolinyl)amino]phenyl]methyl](1-oxododecyl)-amino]-N,N-diethyl-1-piperidinehexanamide, hydrochloride The free base of the title compound can be prepared by the procedure of Example 14 by substituting dodecanoyl chloride for butyric anhydride. The hydrochloride salt is then prepared by dissolving 802 mg (1.12 mmol) of the free base in a mixture of 60 ml of hexane and 10 ml of ethanol. Treatment with 1.1 ml of 1N ethanolic HCl followed concentration in vacuo gave 816 mg of Example 15 (the compound is an amorphous solid which begins to soften at about 50° C): IR (KBr) 3420, 2920, 2840, 1620 cm$^{-1}$; $^1$H NMR (Me$_2$SO-d$_6$, 400 MHz) δ9.1–9.2 (m, 1 H), 8.4 (m, 2 H), 7.9 (m, 1 H), 7.5–7.6 (m, 1 H), 7.2–7.4 (m, 4 H), 6.8–6.9 (m, 1 H), 0.7–4.5 (m, 54 H); MS (+FAB), m/z (rel intensity)=718 (M+H, 100), 452 (23).

Analysis for: $C_{43}H_{64}ClN_5O_2.HCl$; Calculated: C, 68.41; H, 8.68; N, 9.28. Found: C, 68.12; H, 8.79; N, 9.09.

EXAMPLE 17

This assay is employed to identify compounds which compete specifically with tritiated bradykinin ($^3$H-BK) for BK$_2$ receptor sites in guinea pig ileum. Compounds active in this assay are considered bradykinin antagonists useful as analgesic agents.

The assay is carried out as follows:

A 350–500 g adult male Hartley strain guinea pig is euthanized by stunning followed by decapitation. The distal portion of the ileum is removed and placed in ice cold homogenization buffer [25 mM N-tris(hydroxymethyl)methyl-2-aminoethane sulfonic acid (TES) 1 mM 1,10-phenanthroline, adjusted to pH 6.8 with NH$_4$OH]. The contents of the ileal lumen are rinsed out with cold homogenization buffer. The tissue is cut into small pieces and homogenized in 20 volumes of homogenization buffer using a Brinkmann Polytron homogenizer equipped with a PTA 10 TS generator. The tissue is homogenized for 10 seconds, three times, at setting 5.

The homogenate is filtered through a surgical gauze sponge and centrifuged at 50,000×g for 20 minutes at 4° C. The supernatant fluid is discarded and the homogenization and centrifugation procedure is repeated. After discarding the supernatant fluid, the final pellet is resuspended in 40 volumes of assay buffer [25 mM TES, pH=6.8, 1 mM 1,10-phenanthroline, 1 mM dithiothreitol, 2 μM captopril, 140 μg/ml bacitracin and 0.1% bovine serum albumin (BSA)]. The homogenate is filtered once more through a surgical gauze sponge and kept on ice until use.

The assay is performed using only polypropylene pipet tips and polypropylene test tubes. Each tube receives 100 μl of 800 pM $^3$H-BK, 100 μl of the test compound solution or vehicle (TES assay buffer), and 100 μl of 25 mg/ml tissue homogenate in a total volume of 1 ml. The final concentration of $^3$H-BK is 80 pM. The final tissue concentration is 2.5 mg/ml. Compounds are screened at 100 μM. Nonspecific binding is determined in the presence of 1 μM unlabeled bradykinin. All determinations are made in triplicate. Three 100 μl aliquots of the 800 pM $_3$H-BK working solution are added directly to scintillation vials to determine the total added radioactivity.

The tubes are incubated for 90 minutes at 25° C. while being gently agitated on an orbital shaker. Bound ligand is separated from free ligand, using Whatman GF/B glass fiber filters (pretreated with 0.1% aqueous polyethyleneimine made neutral with HCl). A Brandel receptor binding harvester is used. Assay tubes and glass fiber filters are rinsed three times with 3 ml of cold physiological saline.

The filter discs are transferred to 20 ml scintillation vials. Ten ml of aqueous sample LSC cocktail (Aquassure, New England Nuclear) is added to each vial. After capping, the vials are agitated for 5 minutes on an orbital shaker. The samples are counted for ten minutes in a refrigerated liquid scintillation counter.

The following values are obtained:

$B_t$ Total Binding $B_{ns}$ Nonspecific binding $B_x$ Total binding in the presence of the test compound C Control specific binding. $C = B_t - B_{ns}$ D Specific binding in the presence of the test compound. $D = B_x - B_{ns}$ Percent of control: D/C×100
Percent Inhibition: (1−D/C)×100

If 50% inhibition is obtained at the screening concentration, the compound is considered to be active and a dilution series (typically 1:3 serial dilutions of the test compound) is tested in the binding assay. After calculation of Percent of Control for each dilution, the values are analyzed and the IC$_{50}$ with its 95% confidence limits is determined on a Hewlett Packard 9816 computer using the program "PS-NONLIN" (generalized non-linear regression with inverse prediction and graphics).

Compounds which are not soluble in water are first solubilized in DMSO then diluted 1:100 in the assay buffer. Addition of 100 μl of this sample to the assay will yield a final DMSO concentration of 0.1% which has been shown not to affect the binding assay.

| Reference Compounds: | | |
|---|---|---|
| Des Arg$^9$—BK | BK$_1$ Agonist | No Activity |
| DesArg$^9$—Leu$^8$BK | BK$_1$ Antagonist | No Activity |
| | | IC$_{50}$ |
| DPhe$^7$—BK | BK$_2$ Antagonist | 62 nM |
| Thi$^{5,8}$—DPhe$^7$—BK | BK2 Antagonist | 69 nM |
| DArg$^0$—Hyp$^{2,3}$—DPhe$^7$—BK | BK2 Antagonist | 38 nM |
| DArg$^0$—Hyp$^3$—Thi$^{5,8}$—DPhe$^7$—BK | BK2 Antagonist | 14 nM |
| DArg$^0$—Hyp$^3$—DPhe$^7$—BK | BK2 Antagonist | 30 nM |

When tested in this assay, the compounds of the invention gave the following results:

| Compound of Example No. | IC$_{50}$, μM |
|---|---|
| 1 | 8.4 |
| 2 | 6.0 |
| 3 | 10.8 |
| 4 | 2.0 |
| 5 | 1.6 |
| 6 | 4.3 |
| 7 | 2.4 |
| 8 | 1.2 |
| 9 | 0.77 |
| 10 | 4 |
| 11 | 2.5 |
| 12 | 2.7 |
| 13 | 3.9 |
| 14 | 5.5 |
| 15 | 13.8 |
| 16 | 3.8 |

EXAMPLE 18

The assay of this example is used to determine the ability of the compounds of the invention to inhibit the writhing response induced in mice by the exogenous administration of bradykinin. This assay functions as a primary in vivo screen for bradykinin antagonist analgesics.

The assay is carried out as follows:

Male CD-1 mice (14–19 g) are fasted overnight prior to experiment, but have free access to water.

Groups of 10 mice each are used. Each mouse receives an intraperitoneal injection of 1 mg/kg PGE$_2$ (01 ml/10 g body weight) followed 20 minutes later by an i.p. injection of bradykinin 0.5 mg/kg. The number of writhes per mouse is determined for 2 minutes after bradykinin injection. Drugs are given either orally 1 hour prior to bradykinin or i.p. 2 minutes prior to BK (if the drugs are peptides). For primary screen, non-peptidic drugs are administered orally at 20 mg/kg whereas peptides are given i.p. at 10 mg/kg.

The percent inhibition of writhing obtained is calculated as follows:

$$100 \times \frac{C - D}{C}$$

C = mean number of writhes in the control group.
D = mean number of writhes in the drug group.

If 30% inhibition of writhing or higher is observed with the screening dose, the test compounds is considered to be active. Several logarithmically spaced doses will be tested and the ED$_{50}$ (dose which inhibits the writhing response by 50%) will be determined by regression methods with inverse prediction.

PGE$_2$ is dissolved in phosphate buffered saline, bradykinin acetate and soluble drugs in saline. Insoluble drugs are suspended in 0.5% Tween 80.

| Reference Compounds: Compound | ED$_{50}$ mg/kg (i.p. or p.o.) |
|---|---|
| Ibuprofen | 43% inhibition (at 200 mg/kg p.o.) |
| Ketoprofen | 52% inhibition (at 100 mg/kg p.o.) |
| Acetaminophen | 20% inhibition (at 300 mg/kg p.o.) |
| NOVA 349 | 0.6 (i.p.) |
| NOVA 567 | 0.1 (i.p.) |
| Morphine | 4.5 (p.o.) |

When tested in this assay, the compounds of the invention gave the following results:

| Compound of Example No. | % Inhibition at 30 mg/kg i.p.* | % Inhibition at 200 mg/kg p.o.** |
|---|---|---|
| 1 | 13.1 | 7.1 |
| 2 | 51.0 | 26.0 |
| 4 | 40.0 | — |
| 5 | 85.0 | 27.0 |
| 6 | 68.0 | — |
| 7 | 44.0 | — |
| 8 | 80.0 | 58.0 |
| 9 | 0.0 | — |
| 10 | 2.5 | — |
| 11 | 37 | — |
| 12 | 5 | — |
| 13 | 43 | — |
| 14 | 81 | 46 |
| 15 | 43 | — |
| 16 | 30 | — |

*i.p. = intraperitoneally administered test compound
**p.o. = perorally administered test compound

What is claimed is:
1. A compound having the formula

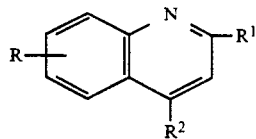

wherein

R is hydrogen, halo or trifluoromethyl
R¹ is hydrogen or X;
R² is hydrogen or X; with the proviso that when R¹ is X, R² is hydrogen, and when R¹ is hydrogen, R² is X;
X is the moiety

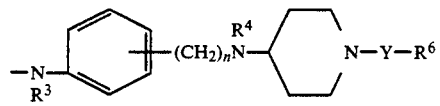

wherein

R³ is hydrogen or lower alkyl;
R⁴ is hydrogen or

R⁵ is hydrogen, lower alkyl, phenyl, phenylloweralkyl or perfluoroloweralkyl;
Y is CO or a bond;
R⁶ is lower alkyl, cycloloweralkyl, arylalkyl, —(CH₂)ₘ-cycloloweralkyl

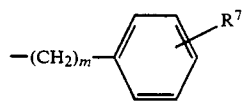

or —(CH₂)ₒCONR⁸R⁹ or, in the case when Y is CO, R⁶ is phenyl;
R⁷ is hydrogen or

R⁸ and R⁹ are, independently, hydrogen, lower alkyl or cycloloweralkyl;
m is 1–3;
n is 1–3;
o is 1–10;
and the pharmacologically acceptable salts thereof.

2. A compound of claim 1, having the formula

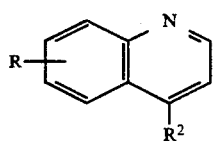

wherein

R is hydrogen, halo or trifluoromethyl;
R² is the moiety

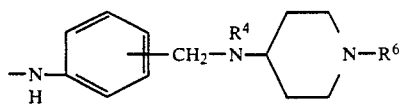

wherein
R⁴ is hydrogen or

R⁵ is hydrogen, alkyl of 1–16 carbon atoms, phenyl, phenylloweralkyl or perfluoroloweralkyl;
R⁶ is lower alkyl, cycloloweralkyl, arylalkyl, —(CH₂)ₘ-cycloloweralkyl or

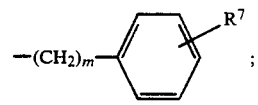

R⁷ is hydrogen or

R⁸ and R⁹ are, independently, hydrogen, lower alkyl or cycloloweralkyl;
m is 1–3;
and the pharmacologically acceptable salts thereof.

3. A compound of claim 1, having the name N-[4-[[(1-butyl-4-piperidinyl)amino]methyl]phenyl]-7-chloro-4-quinolinamine.

4. A compound of claim 1, having the name N-(1-butyl-4-piperidinyl)-N-[[4-[(7-chloro-4-quinolinyl)amino]phenyl]methyl]acetamide.

5. A compound of claim 1, having the name N-(1-butyl-4-piperidinyl)-N-[[4-(4-quinolinylamino)phenyl]methyl]acetamide.

6. A compound of claim 1, having the name N-(1-butyl-4-piperidinyl)-N-[[4-[7-chloro-4-quinolinyl)amino]phenyl]methyl]benzamide.

7. A compound of claim 1, having the name N-(1-butyl-4-piperidinyl)-N-[[4-[(7-chloro-4-quinolinyl)amino]phenyl]methyl]benzenepropanamide.

8. A compound of claim 1, having the name N-(1-butyl-4-piperidinyl)-N-[[4-[(7-chloro-4-quinolinyl)amino]phenyl]methyl]-2,2,3,3,4,4,4-heptafluorobutanamide.

9. A compound of claim 1, having the name N-(1-butyl-4-piperidinyl)-N-[[4-[(7-chloro-4-quinolinyl)amino]phenyl]methyl]-2,2,2-trifluoroacetamide.

10. A compound of claim 1, having the name N-(1-butyl-4-piperidinyl)-N-[[4-[(7-chloro-4-quinolinyl)amino]phenyl]methyl]butanamide.

11. A compound of claim 1, having the name 4-[[4-[[[4-[(7-chloro-4-quinolinyl)amino]phenyl]methyl]amino]-1-piperidinyl]methyl]-N,N-diethylbenzamide.

12. A compound of claim 1, having the name 7-chloro-N-[4-[[[1-(phenylmethyl)-4-piperidinyl]amino]methyl]phenyl]-4-quinolinamine.

13. A compound of claim 1, having the name N-[[4-[(7-chloro-4-quinolinyl)amino]phenyl]methyl]-N-[1-(phenylmethyl)-4-piperidinyl]butanamide.

14. A compound of claim 1, having the name 4-[[4-[[[4-[(7-chloro-4-quinolinyl)amino]phenyl]methyl](1-oxobutyl)amino]-1-piperidinyl]methyl]-N,N-diethylbenzamide.

15. A compound of claim 1, having the name 4-[[[4-[(7-chloro-4-quinolinyl)amino]phenyl]methyl]amino]-N,N-diethyl-1-piperidinehexanamide.

16. A compound of claim 1, having the name 4-[[4-[(7-chloro-4-quinolinyl)amino]phenyl]methyl](1-oxobutyl)amino]-N,N-diethyl-1-piperidinehexanamide.

17. A compound of claim 1, having the name 1-benzoyl-N-[[[4-[(7-chloro-4-quinolinyl)amino]phenyl]methyl]-4-piperidinanamine.

18. A compound of claim 1, having the name 4-[[[4-[(7-chloro-4-quinolinyl)amino]phenyl]methyl](1-oxododecyl)amino]-N,N-diethyl-1-piperidinehexanamide.

* * * * *